United States Patent
Gellman

(10) Patent No.: US 8,591,539 B2
(45) Date of Patent: Nov. 26, 2013

(54) EXPANDABLE CONDUIT-GUIDE AND A METHOD FOR APPLYING AND POSITIONING AN EXPANDABLE CONDUIT-GUIDE

(75) Inventor: Barry N. Gellman, North Easton, MA (US)

(73) Assignee: Thoratec LLC, Pleasanton, CA (US)

( * ) Notice: Subject to any disclaimer, the term of this patent is extended or adjusted under 35 U.S.C. 154(b) by 633 days.

(21) Appl. No.: 11/701,277

(22) Filed: Jan. 31, 2007

(65) Prior Publication Data

US 2007/0233172 A1    Oct. 4, 2007

Related U.S. Application Data

(60) Provisional application No. 60/788,366, filed on Mar. 30, 2006.

(51) Int. Cl.
*A61M 29/00* (2006.01)

(52) U.S. Cl.
USPC ........................................ 606/194

(58) Field of Classification Search
USPC ............. 600/184, 463, 469, 18, 36; 623/2.38, 623/2.37, 2.18, 2.11, 1.46, 1.42, 1.35, 1.24, 623/1.16, 1.15, 1.13, 1.11, 1.2, 1.12, 1.53, 623/1.18, 1.19, 1.23, 1.52, 23.64; 606/200, 606/198, 194, 185, 159, 127, 108, 184; 604/9, 7, 6.16, 6.11, 532, 509, 508, 43, 604/167.06, 101.05, 506, 104–109; 128/898; 29/446
See application file for complete search history.

(56) References Cited

U.S. PATENT DOCUMENTS 4,318,401 A * 3/1982 Zimmerman ................ 604/28
4,417,888 A * 11/1983 Cosentino et al. ........... 604/175
(Continued)

FOREIGN PATENT DOCUMENTS

EP    0078565 A1    5/1983
EP    1523948 A1    4/2005
(Continued)

OTHER PUBLICATIONS

Mueller, Xavier M., et al., "Optimized Venous Return of Self-Expanding Cannula: From Computational Fluid Dynamics to Clinical Application;" 2002; *Interactive Cardiovascular and Thoracic Surgery*; vol. 1; pp. 23-27.

(Continued)

*Primary Examiner* — Ryan Severson
*Assistant Examiner* — Tin Nguyen
(74) *Attorney, Agent, or Firm* — Kilpatrick Townsend & Stockton LLP

(57) ABSTRACT

An expandable conduit-guide providing a leak-tight conduit through a skin between an inside of a corpus and an outside of the corpus is disclosed. The conduit-guide includes a body encompassing a lumen extending essentially axially along a center-line, and has a distal-end to be positioned outside of the corpus, and a proximal-end to be positioned inside of the corpus. The body of the conduit-guide is constructed from a braided-wire so that the conduit-guide is capable of actively expanding from a closed diameter to an opened diameter with the placement of the medical device positioned within the lumen (110) and passively collapsing from the opened diameter to the closed diameter upon withdrawal of the medical device under a spring load of the braided-wire. A catheter-sheath and a catheter-sheath-assembly, as well as to a method for applying and positioning an expandable conduit-guide (1), catheter-sheath (8) and a catheter-sheath-assembly (800) are disclosed.

23 Claims, 6 Drawing Sheets

(56) References Cited

U.S. PATENT DOCUMENTS

| | | | |
|---|---|---|---|
| 5,037,427 A * | 8/1991 | Harada et al. | 606/108 |
| 5,312,417 A | 5/1994 | Wilk | |
| 5,431,676 A | 7/1995 | Dubrul et al. | |
| 6,083,257 A * | 7/2000 | Taylor et al. | 623/1.46 |
| 6,136,025 A | 10/2000 | Barbut | |
| 6,156,064 A * | 12/2000 | Chouinard | 623/1.44 |
| 6,485,513 B1 | 11/2002 | Fan | |
| 6,712,842 B1 * | 3/2004 | Gifford et al. | 623/1.13 |
| 6,866,805 B2 | 3/2005 | Hong | |
| 2002/0002360 A1 * | 1/2002 | Orth et al. | 604/506 |
| 2002/0188201 A1 | 12/2002 | Crowley | |
| 2003/0074049 A1 | 4/2003 | Hoganson | |
| 2003/0092984 A1 * | 5/2003 | Weber | 600/434 |
| 2004/0059277 A1 * | 3/2004 | Maguire et al. | 604/6.16 |
| 2004/0103516 A1 * | 6/2004 | Bolduc et al. | 29/446 |
| 2004/0193241 A1 * | 9/2004 | Stinson | 623/1.2 |
| 2004/0199121 A1 * | 10/2004 | Wenchell et al. | 604/167.06 |
| 2005/0033417 A1 * | 2/2005 | Borges et al. | 623/1.46 |

FOREIGN PATENT DOCUMENTS

| | | |
|---|---|---|
| WO | WO 01/37921 A1 | 5/2001 |
| WO | 2004/096095 A2 | 11/2004 |
| WO | WO 2004096095 A2 * | 11/2004 |
| WO | 2005/002454 A1 | 1/2005 |

OTHER PUBLICATIONS

Office Action for U.S. Appl. No. 11/701,149 dated Feb. 4, 2009.

* cited by examiner

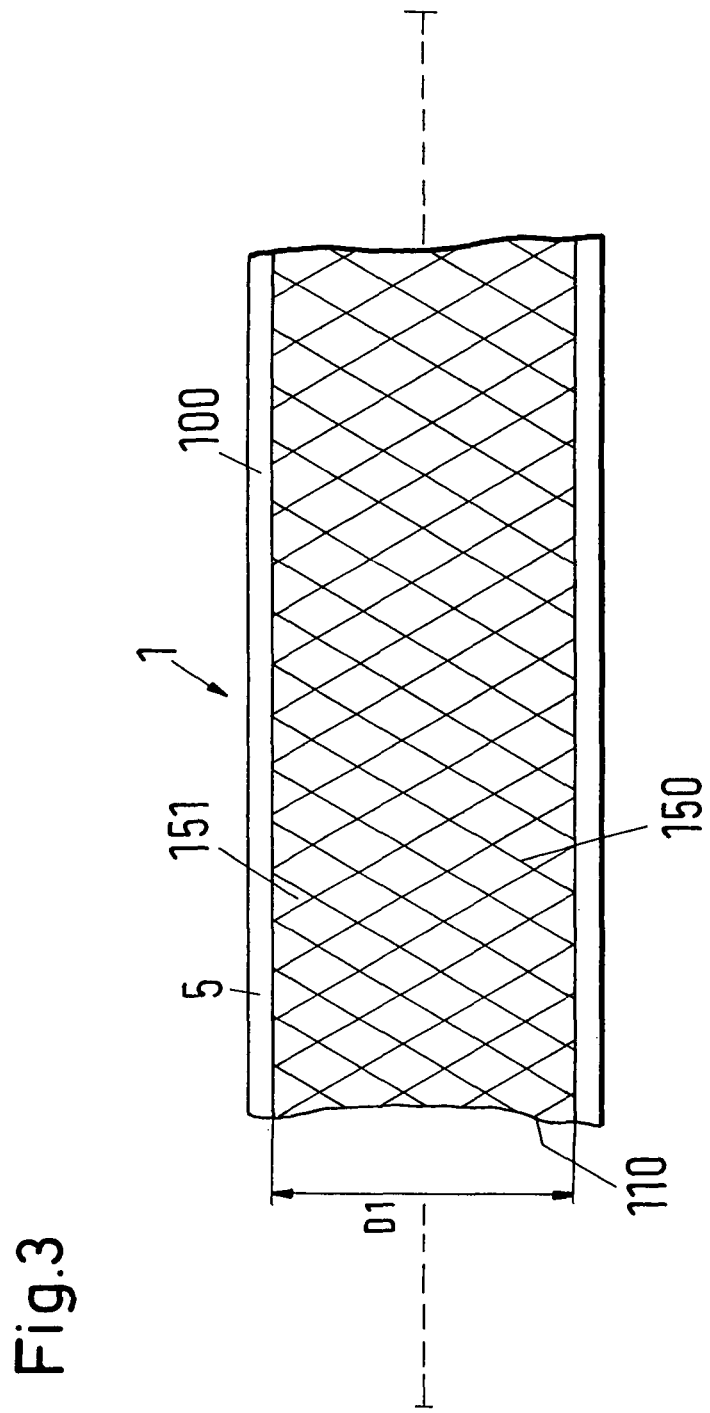

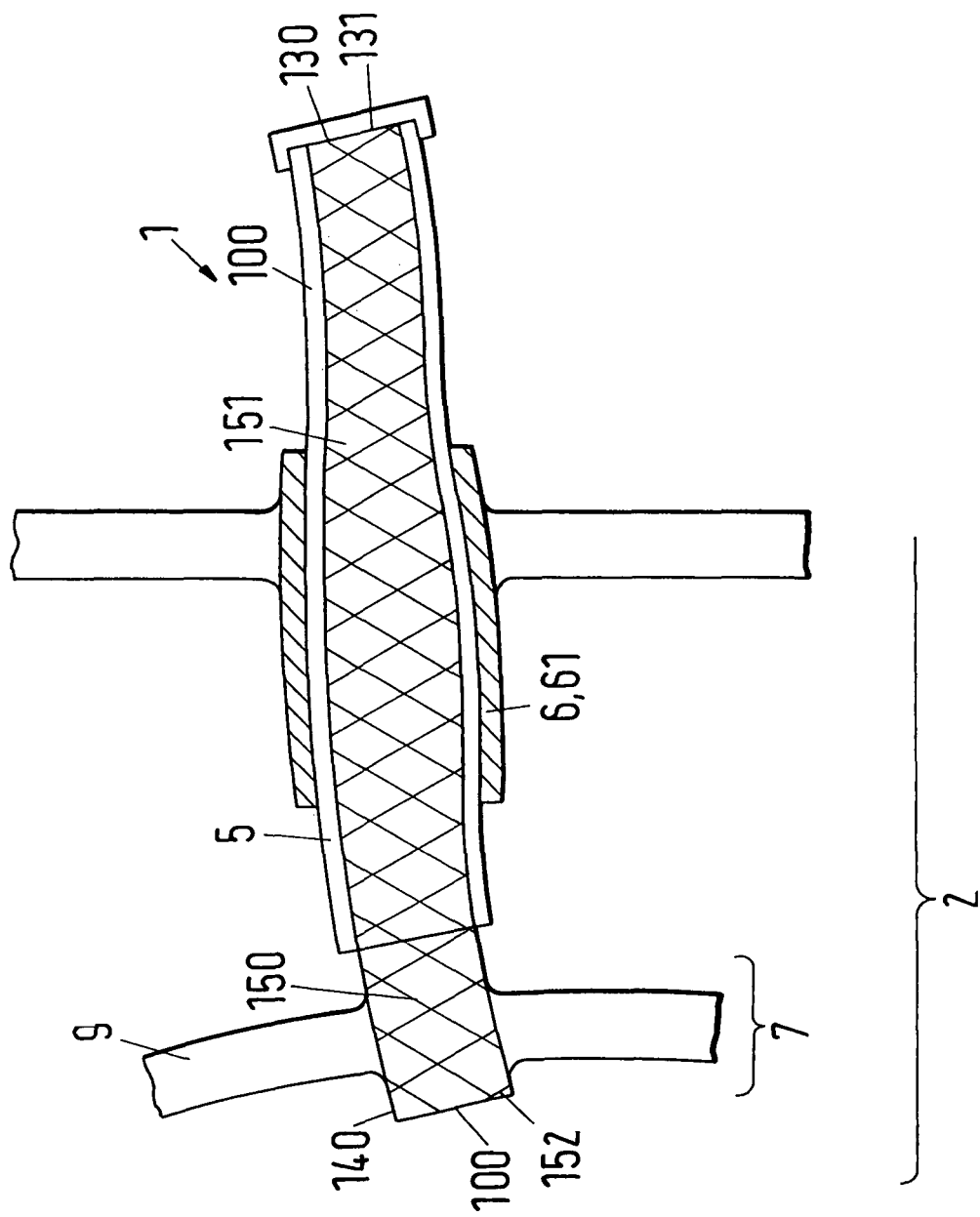

EXPANDABLE CONDUIT-GUIDE AND A METHOD FOR APPLYING AND POSITIONING AN EXPANDABLE CONDUIT-GUIDE

CROSS-REFERENCES TO RELATED APPLICATIONS

This application claims the benefit of U.S. Provisional Application No. 60/788,366, filed Mar. 30, 2006, the disclosure of which is incorporated herein by reference.

BACKGROUND OF THE INVENTION

The invention relates to an expandable conduit-guide, a catheter-sheath, a catheter-sheath-assembly and a method for applying an expandable conduit-guide, a catheter-sheath and a catheter-sheath-assembly.

This disclosure provides a means to enable percutaneous access for a medical device, in particular to exchange cannulae positioned in the heart and/or major vessels and/or other organs utilized for extracorporeal communication of fluid or diagnostic/therapeutic devices. The device proposed by the present invention provides a conduit-guide communicated between the fluid supply extending outside of the body. The conduit-guide enables the passage of a medical device, in particular of a cardiac cannula in and out of the body while effecting a fluid seal during the exchange.

Medical devices such as cardiac cannulae or other medical devices are typically placed under direct vision into major blood vessels and/or the heart of a patient for the purpose of providing a fluid conduit to and from an extracorporeal circuit.

The most common techniques used in Cardiac Surgery Centers for postcardiotomy support include Extracorporeal Membrane Oxygenation (ECMO) and Ventricular Assist Devices (VAD). Poor ventricular function may be diagnosed preoperatively or may have resulted from myocardial insult during surgery (i.e. inadequate perfusion, crossclamping for extended periods of time limiting reperfusion, injury, etc.). Reduced cardiac output will affect other organs due to low blood pressure and blood flow.

Over time, allowing the myocardium to rest may allow recovery. Otherwise, the patient may require long-term cardiac support. Patients who cannot be weaned from cardiopulmonary bypass and possess isolated ventricular dysfunction are probably candidates for a Ventricular Assist Device (VAD). BiVAD support will require two-pump circuits. When pulmonary dysfunction occurs, the patient is most likely a candidate for ECMO.

Cardiac cannulae provide the patient interface means to an extracorporeal blood circuit. Placement of these cannulae may access the vasculature through major vessels (Right Atrium (RA), Left Atrium (LA), Left Ventricular Apex (LVA), Femoral Artery (FA), Femoral Vein (FV), Superior Vena Cava (SVC), Inferior Vena Cava (IVC) or the Aorta). Two cannulae are required in the extracorporeal circuit—one for blood outflow and one for blood return.

The blood outflow cannula is passed through a dilated tunnel created from the ventricle through the subcutaneous plane to the percutaneous access site. The blood return cannula is passed through a dilated tunnel created from the arch of the ascending aorta through the subcutaneous plane to the percutaneous exit site. The percutaneous access sites are located ipsilaterally, on the left abdominal wall for the LVAD, in the medial anterior position. The location is ipsilateral on the right abdominal wall for an RVAD, in the medial anterior position.

The extracorporeal system is attached to the cannulae using good perfusion technique.

Cannulae placed within the thorax are typically secured in place to prevent accidental dislodgement which could result in a catastrophic condition. Purse-string sutures and stabilizer grommets often provide security until tissue healing occurs. As such, removal, and/or exchange of other medical devices, require a second surgery under direct visualization. The open chest wound is closed upon successfully administering the support system.

A problem, which is up to now not yet solved in a satisfactory way, is that the medical devices, which must be introduced into and tunneled through the tissue of the corpus of the patient to get access to the heart, an associate vessel or to another organ, very often have a comparatively large diameter and/or may have an inappropriate surface, for example a rough surface. Among further things, both can affect the skin, tissue or the respective organs to be accessed very negatively and can cause lasting injuries.

SUMMARY OF THE INVENTION

It is therefore an object of the present invention to provide a device and a method for tunneling and positioning a medical device, in particular a cardiac cannula, in a corpus of a patient, enabling a very easy access to an organ in a very conservative manner.

The subject matter of the invention which satisfies these objects is characterized by the features disclosed herein.

Other features relate to particularly advantageous embodiments of the invention.

The invention thus relates to an expandable conduit-guide providing a leak-tight conduit through a skin between an inside of a corpus and an outside of the corpus. The conduit-guide includes a body encompassing a lumen extending essentially axially along a center-line, and has a distal-end to be positioned outside of the corpus, and a proximal-end to be positioned inside of the corpus, so that a medical device can be placed in and passed through the lumen between the distal-end and the proximal-end. The body of the conduit-guide is constructed from a braided-wire so that the conduit-guide is capable of actively expanding from a closed diameter to an opened diameter with the placement of the medical device positioned within the lumen and passively collapsing from the opened diameter to the closed diameter upon withdrawal of the medical device under a spring load of the braided-wire.

The expandable conduit-guide in accordance with the present invention is essentially a wire braided tube covered with a flexible membrane so as to effect a leak-tight conduit-guide capable of actively expanding with the placement of e.g. a cannula or another medical device positioned within its lumen and passively collapsing upon withdrawal of the cannula or another medical device, under spring load and tissue compression.

The conduit-guide is preferably positioned under direct visualization at the time of the medical device placement during open surgery with the proximal end of the conduit-guide for example positioned in a wall of a heart or major vessel of a human patient or an animal, the body of the device tunneled in the corpus of the patient or the animal and a distal-end emerging through the skin to externally communicate the lumen. The device is "normally closed"; that is, it has a small closed diameter requiring minimal tissue puncture due to the small device profile.

Passaging a medical device, e.g. a blood cannula or another medical device, through the lumen of the conduit-guide in accordance with the present invention, the conduit-guide is actively dilated with the passage of the medical device through the lumen and into a heart, vessel or another organ of the patient.

Upon removal of the medical device, the heart muscle or the vessel wall, a diaphragm and/or the skin constrict to assist the spring return conduit-guide to collapse.

That is, using a conduit-guide in accordance with the present invention allows to apply and position a medical device within a human or an animal corpus in a very easy and conservative way, because before positioning the medical device within the corpus, which medical device may have a comparatively considerable diameter and/or may have an inappropriate surface which may affect negatively the tissue and/or the skin and/or an organ by tunneling through, the conduit-guide, having in a closed state a comparatively small closed diameter, is first positioned within the corpus of the patient, only requiring a small tunnel through the skin and the tissue of the corpus due to the small diameter of the conduit-guide in the closed state. After having positioned the conduit-guide within the corpus, the medical device can be tunneled though the conduit-guide in a very conservative manner because the medical device will essentially not get in touch with the tissue and/or the skin during tunneling and, thus, the corpus of the patient will nearly not be negatively affected by applying and positioning the medical device within the corpus.

In a special embodiment which is very important in practice, a pre-determinable portion of the braided-wire is covered by a flexible membrane, which is preferably an elastomeric material creating a membrane-like structure, enabling the braided-wire to articulate from the closed diameter to the opened diameter and the flexible membrane sealing an interstitial space resultant between the braid openings. A further important advantage of the flexible membrane is that the conduit-guide can be tunneled through the skin, the tissue and a wall of the heart, the vessel or a wall of an organ of a patient in a very conservative and easy manner because, due to the flexible membrane, the surface of the conduit-guide becomes smooth and very tissue-friendly.

Regarding another embodiment of the present invention, in the applied state, a pre-determinable velour-portion of the conduit-guide emerging through the skin of the corpus is contained within a velour-like tube to enable a tissue in-growth of the skin, in particular to reduce bacterial wicking about the wound, and/or the velour material is knitted and/or woven polyester and/or the velour-portion is bonded as a velour-tube to an outside diameter of the conduit-guide. A knitted material structure will expand and contract more easily than a woven structure and would be preferred at the skin site. The velour tube is preferably bonded to the outside diameter of the conduit-guide.

In a special embodiment, the proximal-end of the conduit-guide includes a bare-section which does not contain the flexible membrane in order to permit tissue in-growth about the braided-wire, in particular to provide a means for anchoring the conduit-guide and/or the bare-section ranges from 0" to 0.5", in particular from 0" to 0.1", preferably from 0" to 0.25" from a proximal tip of the conduit-guide. In case that the proximal end of the conduit-guide will not contain the membrane on the outside, tissue in-growth is permitted about the wires to provide a means for conduit-guide anchoring. In the bare-section the individual wire is individually coated. In another embodiment, a coating about the individual wires may not be present.

A distal wire-end of a conduit-guide in accordance with the present invention is closed-ended, in particular closed-ended accomplished by a fold of the wire, and/or includes a welded joint end or a coating, especially a polymer coating joining the wire.

The flexible membrane, and/or the closed-ended distal wire-end accomplished by a fold of the wire and/or including a welded joint end and/or the coating, and/or the polymer coating joining the wire, is fabricated from polyurethane and/or vinyl and/or a thermoplastic rubber and/or a natural rubber and/or a thermoset material, in particular silicone, and/or the flexible membrane is dip molded and/or blown film and/or extruded and/or injection molded and/or pultruded and/or assembled from flat stock as a separate component and/or assembled to the braided body, and/or the flexible membrane is applied about the braided-wire by dipping and/or by coating the braided-wire with liquid polymer and/or the flexible membrane is spray applied to the braided-wire. The preferred material for the flexible membrane is silicone resisting complete compression set after indwelling time in the corpus.

In an un-compressed state, a lumen-diameter of the conduit-guide is between 0.1" and 1", in particular between 0.25" and 0.75", preferably about 0.5" and/or wherein the wire is braided to a loose pitch ranging from 0.5" to 4", in particular from 0.75" to 3", especially from 1" to 2" and/or preferably a target length of the wire is 1.5" pitch for a compressed diameter and/or wherein in a compressed state the lumen-diameter ranges from 0.03" to 0.15", in particular from 0.06" to 0.10", preferably about 0.08".

The wire may be braided to a loose pitch ranging from 0.5" to 4", preferably ranging from 1" to 2" with the target length being 1.5" pitch for a compressed diameter.

To avoid misunderstandings, it is noted that the dimension unit 1" is used in the usual way, that is 1"=1 in=1 inch, which equals 2.54 cm.

The number of wires utilized in the over-under braid preferably, but not necessarily, ranges from 5 to 100 wires, in particular from 20 to 48 wires, preferably from 24 to 32 wires, and/or wherein about half of the wires are left-hand wind and about half of the wires are right-hand wind and/or a wire-diameter of a strand is between 0.001" to 0.02", in particular 0.003" to 0.01, preferably about 0.005", and/or the wire is made of plastic, and/or made of a composite material, and/or made of a metal, especially made of a stainless steel, preferably made of at least ½ hard stainless steel.

It is understood that the pitch, wire diameter, number of wires, braid pattern, compressed diameter, and expanded diameter are not limited to these dimensions and will be a function of tightness of braid resultant dimensions desired, strength of spring rate of the coil and other important parameters.

In a further important embodiment, the conduit-guide in accordance with the present invention is pre-assembled at a certain diameter into a catheter-sheath wherein the catheter-sheath may or may not include a depth-marker, in particular a depth-marker-band for positioning a proximal-end of the catheter-sheath in the corpus of a human patient or an animal and/or the catheter-sheath includes a pusher-device for the removal of the catheter-sheath after positioning the conduit-guide within the corpus.

Thus, the conduit-guide in the compressed state is preferably pre-assembled into the catheter-sheath. Contained within the catheter-sheath can also be a pusher-device for sheath removal once the assembly is positioned within the body and the distal-end externalized. Placement of the conduit-guide would be performed with the catheter-sheath in place. It is envisioned that the catheter-sheath would be placed within the body cavity and the distal-end tunneled to emerge out the desired percutaneous site. Once accomplished, e.g. the heart (or major vessel) would be entered by poking the device through the wall. Depth placement for positioning of the proximal end will be identified by marker bands about the catheter-sheaths.

The invention also relates to a catheter-sheath for pre-assembling a conduit-guide as described above in great detail.

In a special embodiment, the catheter-sheath includes a pusher-device for removal of the conduit-guide after positioning the conduit-guide within a human or an animal corpus and/or includes a depth-marker, in particular a depth-marker-band for positioning a proximal-end of the catheter-sheath in the corpus.

Furthermore, the invention relates to a catheter-sheath-assembly including a catheter-sheath as already described.

The invention relates also to a method for applying and positioning an expandable conduit-guide within a human or an animal corpus, and/or a method for positioning a catheter-sheath, and/or a method for positioning a catheter-sheath-assembly in accordance with the present invention, including the following steps:

providing a conduit-guide in accordance with the present invention;

positioning a proximal-end of the conduit-guide in a wall of a heart and/or a major vessel;

tunneling a distal-end of the conduit-guide through a skin of the corpus to externally communicate a lumen of the conduit-guide;

and/or including the following steps:

providing a conduit-guide in accordance with the present invention;

tunneling a distal-end of the conduit-guide through a skin of the corpus to externally communicate a lumen of the conduit-guide;

positioning a proximal-end of the conduit-guide in a wall of a heart and/or a major vessel.

In a special embodiment of a method in accordance with the present invention, a medical device is placed in and/or passed through the lumen of the conduit-guide and/or the conduit-guide is actively dilated with the passage of the medical device through the lumen.

Preferably, on removing the medical device from the conduit-guide, the conduit-guide is collapsed.

In another embodiment of a method according to the present invention, which is very important in practice, the conduit-guide is pre-assembled into a catheter-sheath forming a catheter-sheath-assembly, wherein, especially, the catheter-sheath-assembly is placed within a corpus-cavity, a distal-end of the catheter-sheath-assembly is tunneled to emerge out the desired percutaneous site of the corpus, a heart and/or an associated vessel, in particular a major vessel is entered by poking the catheter-sheath-assembly and/or the conduit-guide tunneled through a wall of the heart and/or the associated vessel and/or a proximal-end of the catheter-sheath-assembly and/or of the conduit-guide is positioned by using a depth-marker, in particular a depth-marker-band, provided about the catheter-sheath.

Preferably, but not necessarily, the catheter-sheath includes a pusher-device and the catheter-sheath is removed by the pusher-device once the conduit-guide is positioned within the corpus and/or once the distal-end of the conduit-guide is externalized.

In a further embodiment, the proximal-end of the conduit-guide is fixed by a suture at a wall of the heart and/or of an associate vessel and/or at a tissue of the corpus.

The medical device is preferably a cannula, in particular a cardiac cannula providing a blood conduit between a major blood vessel and/or an external device, in particular an Extracorporeal Membrane Oxygenation and/or a Ventricular Assist Device and/or a circuit including a blood pump.

The medical device may also be a scope and/or a light and/or a camera and/or another medical device and/or the conduit-guide is provided as a conduit for performing a vision access required for diagnostic and/or therapeutic applications and/or for multi-purpose catheters with vision and/or for therapeutic device access.

With the method in accordance with the present invention, it is also possible to perform an access to a kidney, a bladder, a G.I. tract, in particular to an intestine, a stomach, or an esophagus, to a thorax cavity or to a sinus.

BRIEF DESCRIPTION OF THE DRAWINGS

In the following, the invention will be explained in more detail with reference to the drawings.

FIG. 3 shows a conduit-guide including a flexible membrane;

FIG. 4 shows a conduit-guide according to FIG. 3 in the applied state comprising a velour-portion;

DESCRIPTION OF THE PREFERRED EMBODIMENTS

Figure 1:
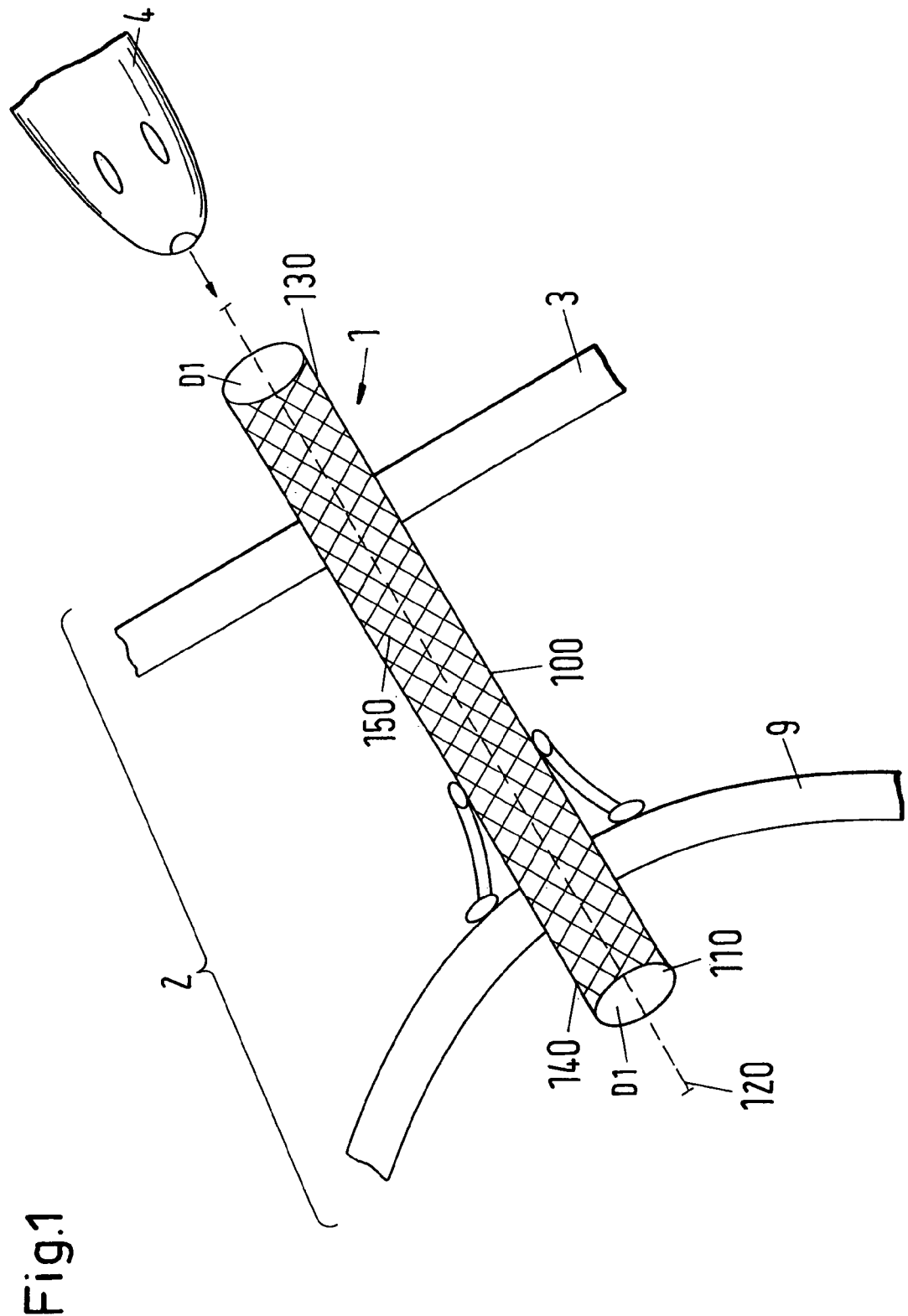
FIG. 1 shows an expandable conduit-guide applied within a patient's corpus.

In FIG. 1 an expandable conduit-guide according to the present invention being applied within a patient's corpus is schematically displayed, which expandable conduit-guide will be designated in the following by the reference number 1.

The expandable conduit-guide 1 providing a leak-tight conduit through a skin 3 between an inside of a corpus 2 and an outside of the corpus 2 includes a body 100 encompassing a lumen 110 extending essentially axially along a center-line 120, and having a distal-end 130 which is in FIG. 1 positioned outside of the corpus 2, and having a proximal-end 140, which is in the example of FIG. 1 positioned inside of the corpus 2 at a wall 9 of a heart of a patient, so that the medical device 4, which is in the present example a cardiac cannula 4, can be placed in and passed through the lumen 110 from the distal-end 130 from the outside of the corpus 2 via the proximal-end 140 through the inside of the corpus 2 and into the heart of the patient to provide a means for a blood exchange between a chamber of the heart and an external device, e.g. to a blood pump, which is not shown in FIG. 1.

Figure 2:
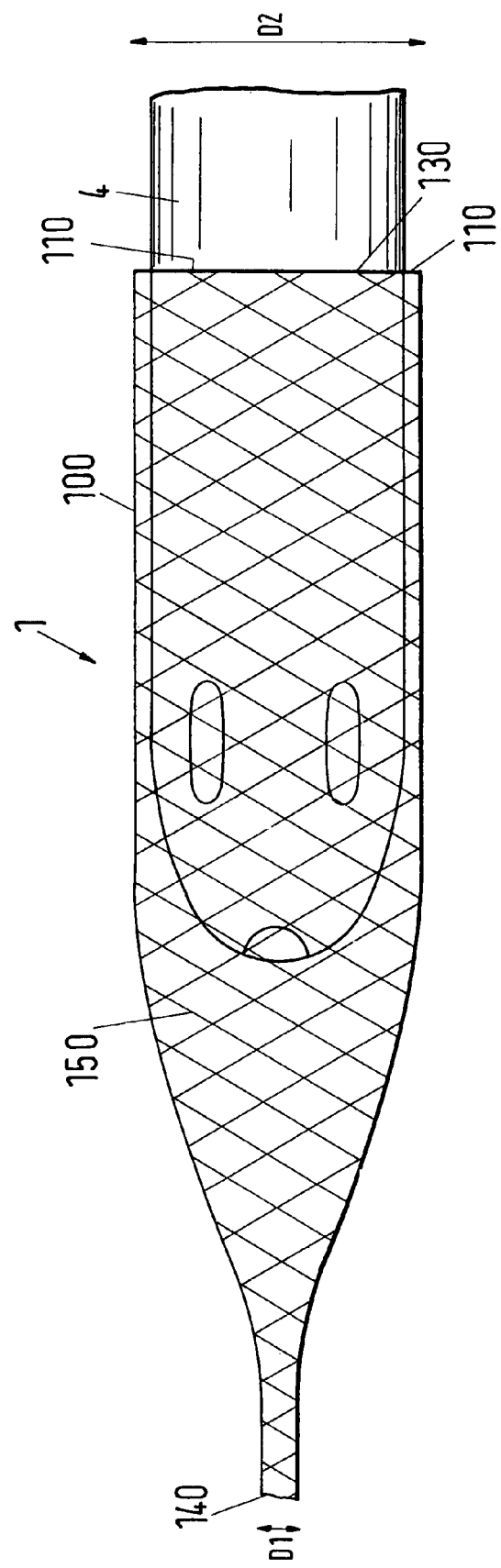
FIG. 2 shows a cardiac cannula actively expanding a conduit-guide.

In FIG. 2 the conduit-guide 1 is displayed in more detail to better explain the co-operation of the conduit-guide 1 with a medical device 4, such as a cardiac cannula 4, as exemplarily shown by FIG. 2. The body 100 of the conduit-guide 1 is constructed from a braided-wire 150, so that the conduit-guide 1 is capable of actively expanding from the closed diameter D1 to the opened diameter D2 with the placement of the medical device 4 positioned within the lumen 110. On the other hand, removing the medical device 4 from the conduit-guide 1 allows the conduit-guide 1 to passively collapse from the opened diameter D2 to the closed diameter D1 upon withdrawal of the medical device 4 under a spring load of the braided-wire 150.

That is, using a conduit-guide 1 in accordance with the present invention allows to apply and position the medical device 4 in a very easy and conservative way. That's why before positioning the medical device 4 within the corpus 2, which medical device 4 has in most cases a comparatively large diameter or can have an inappropriate surface which may affect negatively the tissue or an organ by tunneling through, the conduit-guide 1, having in its closed state a comparatively small closed diameter D1, is first positioned within the corpus 2 of the patient. Due to the small diameter D1 of the conduit-guide 1 in the closed state, the conduit-guide 1 only requires a small tunnel through the skin 3 and the tissue of the corpus 2. After having positioned the conduit-guide 1 within the corpus 2, the medical device 4 can be tunneled to e.g. the heart through the conduit-guide 1 in a very conservative manner because the medical device 4 will essentially not get in touch with the tissue and/or the skin during tunneling and, thus, the corpus 2 of the patient will not be negatively affected by applying and positioning the medical device 4, e.g. a cardiac cannula 4, within the corpus 2.

The embodiment of a conduit-guide 1 shown in FIG. 3 includes a flexible membrane 5. Regarding this embodiment, which is very important in practice, a pre-determinable portion of the body 100 and the braided-wire 150, respectively, is covered by a flexible membrane 5 enabling the braided-wire 150 to articulate from the closed diameter D1 to the opened diameter D2 and, additionally, the flexible membrane 5 seals an interstitial space 151 resultant between the braid openings.

A very important advantage of a conduit-guide 1 according to FIG. 3 having a flexible membrane 5, which is preferably made of an elastomeric material creating the membrane-like structure, is that the conduit-guide 1 can be tunneled through the skin 3, the tissue and a wall 9 of the heart of the patient, or the vessel, or a wall of an organ in a very conservative and easy manner because due to the properties of the flexible membrane 5 the surface of the conduit-guide 1 becomes smooth and very tissue-friendly.

In FIG. 4 a conduit-guide 1 according to FIG. 3 is displayed in the applied state, comprising a velour-portion 6 in a pre-determinable portion of the body 100 of the conduit-guide 1.

In the example of FIG. 4 the pre-determinable velour-portion 6 of the conduit-guide 1 is emerged through the skin 3 of the corpus 2, and is contained within a velour-like tube 61 to enable a tissue in-growth of the skin 3, in particular to reduce bacterial wicking about the wound. Preferably, the velour material is knitted and/or woven polyester and the velour-portion 6 is bonded as a velour-tube 61 to an outside diameter of the conduit-guide 1.

The proximal-end 140 of the conduit-guide 1 includes a bare-section 7 which is placed in the wall 9 of the heart of a patient. The bare-section 7 does not contain the flexible membrane 5 in order to permit tissue in-growth about the braided-wire 150. That provides in particular a means for anchoring the conduit-guide 1 and the bare-section 7, respectively, within the wall 9 of the heart.

Preferably, but not necessarily, in the bare-section 7 the individual wire 152 is individually coated, which is not the case in the example of FIG. 4.

The distal wire-end 131 of the conduit-guide according to FIG. 4 is closed-ended by a welded joint. It is understood that in another embodiment the closed-ended of the distal wire-end 131 can be accomplished by a fold of the wire, and/or may include a welded joint end or a coating, especially a polymer coating joining the wire.

Figure 5A:
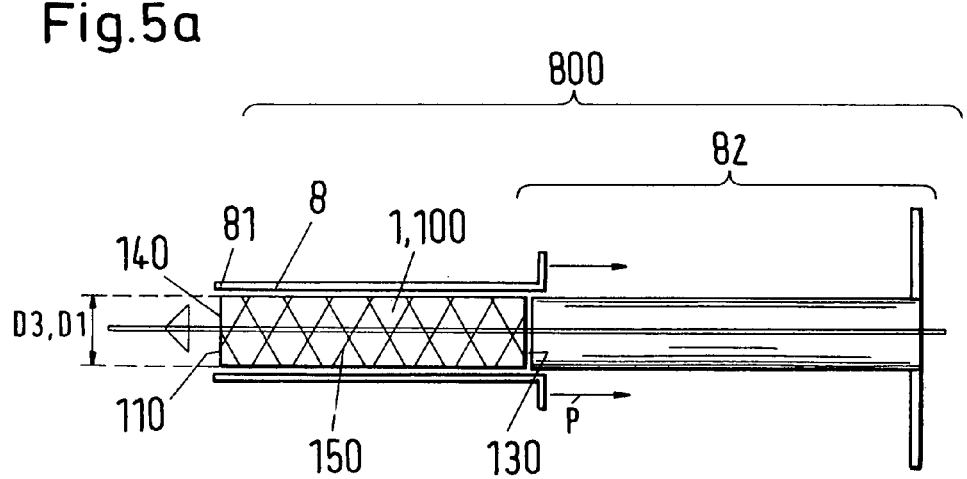
FIG. 5a shows a catheter-sheath-assembly.
Figure 5B:
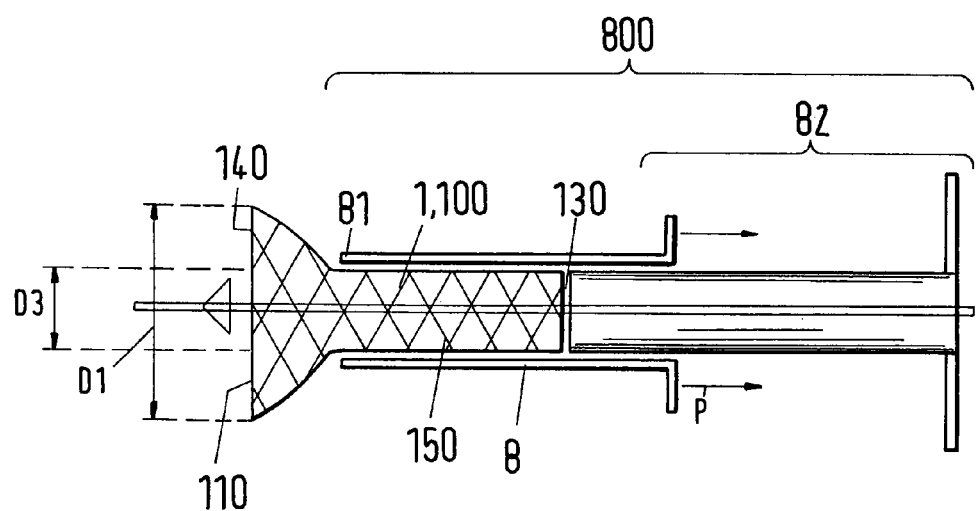
FIG. 5b shows a catheter-sheath-assembly according to FIG. 5a partly removed.
Figure 5C:
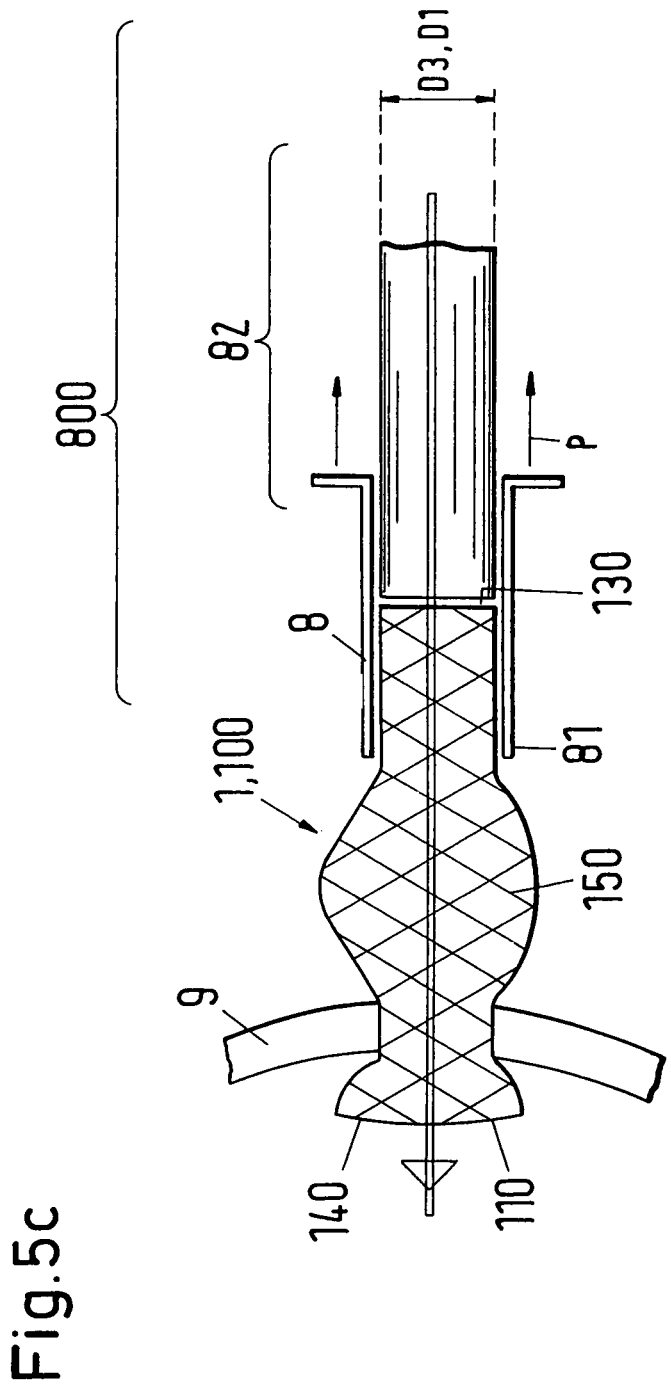
FIG. 5c shows a catheter-sheath-assembly with the conduit-guide being attached to the wall of a heart.

FIGS. 5a-5c show a catheter-sheath-assembly including a conduit-guide 1 assembled in a catheter-sheath 8 having a pusher 82 for removing the conduit-guide 1 after having it positioned within the corpus 2 of a patient.

The catheter-sheath-assembly 800 according to FIGS. 5a and 5b has not been introduced into a corpus 2 yet. The conduit-guide 1 is pre-assembled at a diameter D1, D3 into a catheter-sheath 8, wherein the diameter D3 of the conduit-guide 1 assembled in the catheter-sheath 8 may be equal or not equal to the diameter D1, wherein D3 may be in particular smaller than the diameter D1 of the conduit-guide in the closed state. In a special embodiment, the catheter-sheath 8 may include a depth-marker, in particular a depth-marker-band for positioning a proximal-end 81 of the catheter-sheath 8 in the corpus 2. The special embodiment shown in FIGS. 5a-5c does not include the depth-markers. The catheter-sheath 8 according to FIGS. 5a-5c includes, as already mentioned, a pusher-device 82 for catheter-sheath 8 removal after positioning the conduit-guide 1 within the corpus 2.

Regarding FIG. 5a, the conduit-guide 1 is completely encompassed by the catheter-sheath 8 at a diameter D1, D3 and is ready for positioning within a corpus 2 of a patient.

FIG. 5b demonstrates how the pusher-device 82 works. Moving the pusher-device 82 along the arrow P, the catheter-sheath 8 is removed from the conduit-guide 1 and the conduit-guide 1 will expand to its closed diameter D1, in case that the diameter D3 of the encompassed state is smaller than the diameter D1 of the conduit-guide 1 in its closed state.

Regarding FIG. 5c, the conduit-guide 1 is introduced into the wall 9 of the heart of a patient and the catheter-sheath 8 is partly, but not completely, removed by the pusher-device 82 from the conduit-guide 1 after having positioned the conduit-guide 1 within the wall 9 of the heart.

That is, once the assembly is positioned within the body and the distal-end externalized, placement of the conduit-guide would be performed with the catheter-sheath in place. It is envisioned that the catheter would be placed within the body cavity and the distal-end tunneled to emerge out the desired percutaneous site. Once accomplished, the heart (or major vessel) would be entered by poking the device through the wall.

It is understood that the invention is not only related to the special embodiments discussed above but, of course, further embodiments are included, too. In particular, the invention relates to all advantageous combinations of the discussed embodiments.

The invention claimed is:

1. A combination of an expandable conduit-guide and a medical device, the conduit-guide providing a leak-tight conduit through a skin between an inside of a corpus and an outside of the corpus, said conduit-guide including a body encompassing a lumen, and having a distal end to be positioned outside of the corpus, and having a proximal end to be positioned inside of the corpus, the conduit-guide and the medical device being configured and dimensioned relative to one another so that the medical device can be placed in and passed through the lumen between the distal end and the proximal end of the conduit-guide, wherein the body of the conduit-guide is constructed from a braided wire having a spring load, wherein the body of the conduit-guide is capable of actively expanding the lumen from a closed diameter to an opened diameter and passively collapsing from the opened diameter to the closed diameter, wherein a portion of the braided wire is covered by a flexible membrane enabling the braided wire to articulate from the closed diameter to the opened diameter, wherein the flexible membrane seals an interstitial space resultant between the braid openings, wherein the proximal end of the conduit-guide includes a bare section which does not contain the flexible membrane in order to permit tissue in-growth about the braided wire to provide for anchoring the conduit-guide, wherein the conduit-guide and the medical device are further configured and dimensioned relative to one another so that when the medical device is placed in the lumen, the lumen actively expands, and when the medical device is withdrawn from the lumen, the body of the conduit-guide passively collapses the lumen under the spring load of the braided wire.

2. The combination of claim 1, wherein the conduit-guide further comprises a velour portion configured to emerge through the skin of the corpus when the conduit-guide is positioned with the proximal end inside of the corpus and the distal end outside of the corpus, wherein the velour portion is contained within a velour-like tube.

3. The combination of claim 1, wherein a distal wire end of the conduit-guide is closed-ended by at least one member of the group consisting of: a fold of the wire, a welded joint end, and a coating.

4. The combination of claim 1, wherein the flexible membrane comprises at least one member of the group consisting of polyurethane, vinyl, a thermoplastic rubber, a natural rubber, a thermoset material, and silicone.

5. The combination of claim 1, wherein the closed diameter is between 0.1" and 1".

6. The combination of claim 1, wherein the number of wires utilized in the over-under braid ranges from 5 to 100 wire.

7. The combination of claim 1, further comprising a sheath configured and dimensioned for the conduit-guide to be inserted therein, wherein an interior diameter of the sheath does not exceed an exterior diameter of the conduit-guide when the lumen is at the closed diameter.

8. The combination of claim 7, wherein the sheath comprises a pusher for removal of the conduit-guide after positioning the conduit-guide within the corpus.

9. The combination of claim 1, wherein passively collapsing comprises automatic collapsing of the lumen upon removal of the medical device from the lumen.

10. The combination of claim 1, wherein the bare section ranges from 0" to 0.5" from a proximal tip of the conduit-guide.

11. The combination of claim 1, wherein the spring load is inwardly directed to collapse the lumen from the opened diameter to the closed diameter.

12. The combination of claim 1, wherein individual wires of the braided wire of the bare section are individually coated.

13. The combination of claim 1, wherein the medical device comprises a cannula.

14. The combination of claim 1, wherein the medical device comprises at least one member of the group consisting of a scope, a light, and a camera.

15. A method for positioning a medical device within a human or an animal patient having a skin, the method comprising:
positioning a proximal end of a conduit-guide in or adjacent a wall of the patient,
the conduit-guide comprising a body encompassing a lumen, wherein the body of the conduit-guide is capable of actively expanding the lumen from a closed diameter to an opened diameter and passively collapsing the lumen from the opened diameter to the closed diameter;
positioning a distal end of the conduit-guide through the skin of the patient to externally communicate the lumen of the conduit-guide with an external environment outside of the patient, to thus define an operative position of the conduit-guide, wherein, in the operative position, the proximal end is positioned in or adjacent the wall, and the distal end protrudes through the skin to provide communication of the lumen of the conduit-guide with the external environment outside of the patient; and
when the conduit-guide is in the operative position, introducing the medical device into the conduit-guide, thereby actively expanding the lumen from the closed diameter to the opened diameter.

16. The method of claim 15, further comprising removing the medical device from the conduit-guide, whereby the conduit-guide is collapsed.

17. The method of claim 15, wherein prior to the positioning steps, the conduit-guide is part of an assembly of the conduit-guide encased in a sheath.

18. The method of claim 17, wherein the sheath comprises a pusher-device, the method further comprising removing the sheath by the pusher-device when the conduit-guide is in the operative position.

19. The method of claim 15, further comprising fixing the proximal end of the conduit-guide by a suture to the wall.

20. The method of claim 15, wherein the medical device comprises a cannula.

21. The method of claim 15, wherein the medical device comprises at least one member of the group consisting of a scope, a light, and a camera.

22. The method of claim 15, wherein the wall of the patient is a wall of an organ or a vessel of the patient.

23. The method of claim 22, wherein the organ or the vessel of the patient is the patient's heart.

* * * * *